US009630908B2

(12) United States Patent
Merschaert et al.

(10) Patent No.: US 9,630,908 B2
(45) Date of Patent: *Apr. 25, 2017

(54) PROCESS FOR PREPARING LACOSAMIDE

(71) Applicant: UCB Pharma GmbH, Monheim (DE)

(72) Inventors: Alain Merschaert, Brussels (BE); Christophe Joseph Szczepaniak, Brussels (BE); Joerg Hamann, Köln (DE); Ralf Kanzler, Leverkusen (DE)

(73) Assignee: UCB Pharma GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,954

(22) Filed: Aug. 17, 2015

(65) Prior Publication Data

US 2016/0039744 A1    Feb. 11, 2016

Related U.S. Application Data

(63) Continuation of application No. 13/988,160, filed as application No. PCT/EP2011/069721 on Nov. 9, 2011, now Pat. No. 9,139,513.

(30) Foreign Application Priority Data

Nov. 17, 2010  (EP) ..................... 10191524

(51) Int. Cl.
| | |
|---|---|
| *C07C 231/14* | (2006.01) |
| *C07C 227/34* | (2006.01) |
| *C07C 227/18* | (2006.01) |
| *C07C 237/22* | (2006.01) |
| *C12P 13/06* | (2006.01) |
| *C12P 13/04* | (2006.01) |
| *C07C 231/02* | (2006.01) |
| *C12P 41/00* | (2006.01) |

(52) U.S. Cl.
CPC .......... *C07C 231/02* (2013.01); *C07C 227/18* (2013.01); *C07C 227/34* (2013.01); *C07C 231/14* (2013.01); *C07C 237/22* (2013.01); *C12P 13/04* (2013.01); *C12P 13/06* (2013.01); *C12P 41/007* (2013.01); *C07B 2200/07* (2013.01)

(58) Field of Classification Search
CPC ......... C12P 41/007; C12P 13/06; C12P 13/04; C07C 231/14; C07C 227/34; C07C 227/18; C07C 237/22; C07B 2200/07
See application file for complete search history.

(56) References Cited

U.S. PATENT DOCUMENTS 9,139,513 B2 *  9/2015  Merschaert ............. C12P 13/06

FOREIGN PATENT DOCUMENTS

CN         101591300 A     12/2009

OTHER PUBLICATIONS

Jaeger et al., "Enzymatic Resolution of O-Methyl-N-acetyl-DL-serine", Croatian Chemical Society, 1956, vol. 28, 5-8.
Greenstein et al., "L—isoleucine, D—isoleucine, L—alloisoleucine, and D—alloisoleucine", Biochemical Preparations, 1953, vol. III, 84-103.

* cited by examiner

*Primary Examiner* — Shailendra Kumar
(74) *Attorney, Agent, or Firm* — McDonnell Boehnen Hulbert & Berghoff LLP

(57) ABSTRACT

The present invention provides a process for the preparation of lacosamide in substantially optically pure form, which in one aspect comprises the following steps: (i) resolution of O-methyl-D,L-serine to provide O-methyl-D-serine in substantially optically pure form; (ii) acetylation of O-methyl-D-serine thereby obtained to provide the N-acetyl 10 derivative thereof in substantially optically pure form; (iii) activating the carboxy group of the compound thereby obtained; and (iv) reacting the compound thereby obtained with benzylamine.

6 Claims, No Drawings

PROCESS FOR PREPARING LACOSAMIDE

This application is a continuation of U.S. patent application Ser. No. 13/988,160 filed on Sep. 27, 2013, now U.S. Pat. No. 9,139,513, which is a US national phase of International Application No. PCT/EP2011/069721 filed on Nov. 9, 2011, which claims priority to European Patent Application No. 10191524.7 filed on Nov. 17, 2010, the specification, claims, and drawings (if any) of all of which are hereby incorporated by reference into the specification of this application.

The present invention relates to the preparation of a therapeutically active compound. More particularly, the invention concerns an improved process for manufacturing lacosamide.

Lacosamide, i.e. (R)-2-acetylamino-N-benzyl-3-methoxypropionamide, has been approved for sale as a medicine by regulatory agencies throughout the world. By way of illustration, the US Food and Drug Administration (FDA) and the European Medicines Evaluation Agency (EMEA) have both approved lacosamide as adjunctive therapy in the treatment of partial-onset seizures in patients with epilepsy.

Various methods for preparing lacosamide are known from the prior art. For example, WO 2010/052011 describes a process for manufacturing substantially optically pure lacosamide comprising resolution of 2-acetamido-N-benzyl-3-methoxypropionamide, typically in racemic form, into its (R) and (S) enantiomers; racemisation of the (S) isomer thereby obtained; and further resolution of the resulting 2-acetamido-N-benzyl-3-methoxypropionamide.

WO 2006/037574 describes a method of producing lacosamide comprising the O-methylation of a hydroxy precursor.

The present invention provides an attractive process for manufacturing lacosamide on a commercial scale. Lacosamide is obtained from the process in high chemical and optical purity. The process in accordance with the invention displays significant economic advantages in that it commences from relatively inexpensive starting materials, as well as providing lacosamide in a short sequence of high yielding steps.

Thus, the present invention provides a process for the preparation of lacosamide of formula (I):

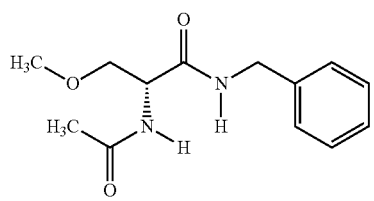
(I)

in substantially optically pure form; which comprises the following steps:
(i) resolution of O-methyl-D,L-serine of formula (II):

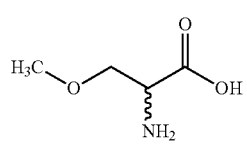
(II)

to provide O-methyl-D-serine of formula (III):

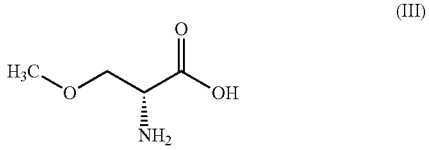
(III)

in substantially optically pure form;
(ii) acetylation of O-methyl-D-serine of formula (III) thereby obtained to provide the compound of formula (IV):

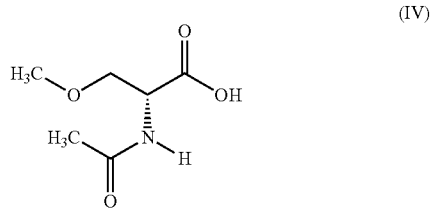
(IV)

in substantially optically pure form;
(iii) activating the carboxy group of the compound of formula (IV) thereby obtained to provide a compound of formula (V):

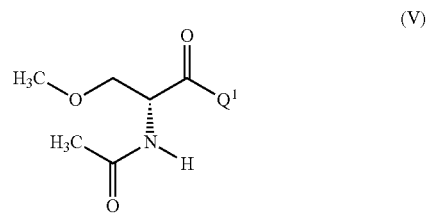
(V)

wherein $Q^1$ represents a carboxy activating group; in substantially optically pure form; and
(iv) reacting the compound of formula (V) thereby obtained with benzylamine.

The expression "substantially optically pure" as used herein when referring to a particular compound means that, in any given sample of that compound, at least 95%, preferably at least 96%, more preferably at least 97%, still more preferably at least 98%, most preferably at least 99%, of a specified chiral centre is in the (R) or (S) configuration.

Therefore, the expression "in substantially optically pure form" in relation to lacosamide means that, in a given sample of lacosamide, at least 95%, preferably at least 96%, more preferably at least 97%, still more preferably at least 98%, most preferably at least 99%, of the 2-acetylamino-N-benzyl-3-methoxypropionamide molecules within the sample are molecules in which the chiral centre is in the (R) configuration.

The process in accordance with the present invention commences from the known compound O-methyl-D,L-serine of formula (II) above. Typical methods for preparing compound (II) are described in *J. Biol. Chem.*, 1936, 793; *J. Biol. Chem.*, 1933, 511; *Org. Synth. Coll.*, 1955, Vol. 3, 774; and references cited therein. Compound (II) is commercially available from a variety of suppliers, including Shanghai Hanhong Chemicals (Shanghai, China) and Manus Aktteva (Ahmedabad, India). Of crucial importance for the present purposes, compound (II) is relatively inexpensive, with a purchase price for manufacturing scale quantities (as at mid-2010) being typically in the region of € 100 per kilogram.

Step (i) of the above-described process comprises the resolution of O-methyl-D,L-serine of formula (II) above to provide O-methyl-D-serine of formula (III) above in substantially optically pure form.

The term "resolution" as used herein refers to the separation of a mixture of enantiomers into its corresponding individual enantiomers. The enantiomers may be present in the mixture in various ratios of one enantiomer versus the opposite enantiomer. Typical ratios of enantiomers according to the present invention range from about 3:97 to 97:3, preferably from about 5:95 to 95:5, more preferably from about 30:70 to 70:30, still more preferably from about 40:60 to 60:40, even more preferably from about 45:55 to 55:45.

In a particular embodiment, the mixture is a racemic mixture, i.e. a mixture comprising 50% of one enantiomer and 50% of the opposite enantiomer.

Resolution may suitably be accomplished by various conventional methods known from the prior art. Such methods may include conversion to diastereoisomers; differential absorption; chiral recognition; biochemical processes; mechanical separation; kinetic resolution; and deracemization. A general description of resolution methods is provided in M. B. Smith & J. March, "*March's Advanced Organic Chemistry*", fifth edition, Wiley-Interscience, 2001, Chapter 4, pages 125-217; in particular pages 151-155. A more detailed description of resolution methods with particular reference to lacosamide is provided in WO 2010/052011.

By way of example, diastereomeric derivatives, e.g. salts, may be produced by reacting the enantiomer mixture of formula (II) with an appropriate chiral compound, e.g. a chiral acid or a chiral base. The resulting mixture of diastereomers may then be separated, followed by regeneration of the desired enantiomer of formula (III). Typically, the enantiomer mixture of formula (II) is treated with a chiral acid; the resulting mixture of diastereomeric salts is separated; then the desired enantiomer of formula (III) is regenerated. Examples of suitable chiral acids include the following:

N-acetyl-D-phenylalanine
N-acetyl-(R)-naphthylalanine
dibenzoyl-D-tartaric acid
(R)-(−)-mandelic acid
N-acetyl-D-glutamic acid
N-benzyloxycarbonyl-D-tyrosine
N-acetyl-D-methionine
(−)-camphanic acid Favourably, the chiral acid is N-acetyl-D-phenylalanine or N-acetyl-(R)-naphthylalanine. In one embodiment, the chiral acid is N-acetyl-D-phenylalanine. In another embodiment, the chiral acid is N-acetyl-(R)-naphthylalanine.

Treatment of the enantiomer mixture of formula (II) with the selected chiral acid is conveniently effected at an elevated temperature, e.g. a temperature in the region of 50° C., in a suitable solvent, e.g. a $C_{1-4}$ alkanol such as methanol or ethanol, optionally in admixture with water. Following separation of the resulting mixture of diastereomeric salts, the desired enantiomer of formula (III) may then be regenerated in high optical purity and good yield by treatment with an acid, then with a base, at controlled pH. The acid is suitably a mineral acid, e.g. hydrochloric acid, and it is added in sufficient quantity to adjust the pH to approximately 1-2. Following extraction of the resulting material into an organic solvent, the pH is adjusted to approximately 7 by treatment with a base, typically an alkali metal hydroxide such as sodium hydroxide, whereby the desired enantiomer of formula (III) is regenerated.

In a particular embodiment, compound (III) may be obtained in substantially optically pure form from compound (II) by means of a process which comprises the following steps:

(i-A) conversion of O-methyl-D,L-serine of formula (II) as depicted above into an ester derivative of formula (VI):

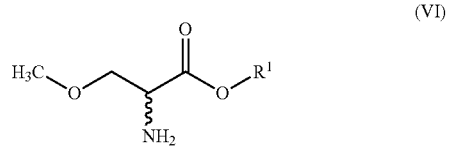

wherein $R^1$ represents aryl($C_{1-6}$)alkyl or heteroaryl($C_{1-6}$)alkyl, either of which groups may be optionally substituted by one or more substituents;

(i-B) resolution of the compound of formula (VI) thereby obtained to provide a compound of formula (VII):

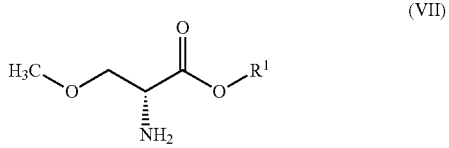

wherein $R^1$ is as defined above; in substantially optically pure form; and (i-C) de-esterification of the compound of formula (VII) thereby obtained.

The expression "($C_{1-6}$)alkyl" as used herein is intended to include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl.

Suitable aryl groups include phenyl and naphthyl, preferably phenyl.

Suitable aryl($C_{1-6}$)alkyl groups include benzyl, phenylethyl, phenylpropyl and naphthylmethyl, preferably benzyl.

Suitable heteroaryl groups include furyl, benzofuryl, dibenzofuryl, thienyl, benzothienyl, dibenzothienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, purinyl, oxadiazolyl, thiadiazolyl, triazolyl, benzotriazolyl, tetrazolyl, pyridinyl, quinolinyl, isoquinolinyl, pyrrolo[2,3-b]pyridinyl, pyrrolo[3,2-c]pyridinyl, pyrazolo[1,5-a]pyridinyl, imidazo[1,2-a]pyridinyl, imidazo[4,5-b]pyridinyl, naphthyridinyl, pyridazinyl, cinnolinyl, phthalazinyl, pyrimidinyl, quinazolinyl, pyrazolo[3,4-d]pyrimidinyl, imidazo[1,2-a]pyrimidinyl, pyrazinyl, imidazo[1,2-a]-pyrazinyl, quinoxalinyl, pteridinyl, triazinyl and chromenyl groups.

In one embodiment, $R^1$ represents aryl($C_{1-6}$)alkyl, which group may be optionally substituted by one or more substituents. In another embodiment, $R^1$ represents heteroaryl($C_{1-6}$)alkyl, which group may be optionally substituted by one or more substituents.

Suitably, $R^1$ represents benzyl, which group may be optionally substituted by one or more substituents.

In one embodiment, $R^1$ is unsubstituted. In another embodiment, $R^1$ is substituted by one or more substituents, preferably by one or two substituents. In one aspect of that embodiment, $R^1$ is monosubstituted. In another aspect of that embodiment, $R^1$ is disubstituted.

Examples of suitable substituents on $R^1$ independently include halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$) alkylaminocarbonyl, amino sulfonyl, $C_{1-6}$ alkylaminosulfonyl and di($C_{1-6}$)alkylaminosulfonyl.

The term "halogen" as used herein is intended to include fluorine, chlorine, bromine and iodine atoms, typically fluorine, chlorine or bromine.

Examples of particular substituents on $R^1$ independently include fluoro, chloro, bromo, cyano, nitro, methyl, ethyl, trifluoromethyl, hydroxy, methoxy, difluoromethoxy, trifluoromethoxy, methylthio, methylsulfinyl, methyl sulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethyl-aminocarbonyl, aminosulfonyl, methyl aminosulfonyl and di methyl aminosulfonyl.

In a particular embodiment, $R^1$ represents benzyl.

Step (i-A) of the above-described process comprises the conversion of O-methyl-D,L-serine (II) into the ester derivative (VI). This transformation may be achieved by reacting O-methyl-D,L-serine (II) with a compound of formula $R^1$-$L^1$, wherein $R^1$ is as defined above, and $L^1$ represents a suitable leaving group.

The leaving group $L^1$ is typically a halogen atom, e.g. bromo.

The reaction is conveniently effected under basic conditions, typically in the presence of an inorganic base, suitably an alkali metal carbonate or bicarbonate, e.g. sodium carbonate, potassium carbonate, sodium bicarbonate or potassium bicarbonate (see, for example, *Letters in Organic Chemistry*, 2010, 7, 39-44).

Alternatively, the ester derivative (VI) may be prepared by reacting O-methyl-D,L-serine (II) with a compound of formula $R^1$—OH, wherein $R^1$ is as defined above. The reaction is conveniently effected under acidic conditions, i.e. by bringing the reactants together in the presence of a strong acid, optionally at an elevated temperature. Suitable acids include p-toluenesulphonic acid (see, for example, *European Journal of Medicinal Chemistry*, 2010, 45, 1717-1723; and *Tetrahedron*, 2009, 65, 9702-9706) and hydrochloric acid (see, for example, *Synthesis*, 2009, 2184-2204).

Step (i-B) of the above-described process comprises the resolution of compound (VI) to provide compound (VII) in substantially optically pure form. As acknowledged above, resolution may suitably be accomplished by various conventional methods known from the prior art.

Typically, the enantiomer mixture of formula (VI) is treated with a chiral acid; the resulting mixture of diastereomeric salts is separated; then the desired enantiomer of formula (VII) is regenerated. Examples of suitable chiral acids include N-acetyl-L-leucine, N-acetyl-L-methionine and N-acetyl-L-glutamine.

In a particular embodiment, the enantiomer mixture of formula (VI) is treated with N-acetyl-L-methionine. Separation of the resulting mixture of diastereomeric salts is then followed by regeneration of the desired enantiomer of formula (VII). The reaction between compound (VI) and N-acetyl-L-methionine is conveniently effected by stirring the reactants in a suitable solvent, typically an organic solvent such as 4-methyl-2-pentanone (methyl isobutyl ketone). After separation of the resulting mixture of diastereomeric salts, regeneration of the desired enantiomer (VII) may be accomplished by treating an aqueous solution of the material thereby obtained with an alkaline solution, typically an aqueous solution of an inorganic base, e.g. an alkali metal carbonate such as sodium carbonate. By proceeding in this manner, the desired enantiomer of formula (VII) may be obtained in high yield, and high chemical and optical purity.

Step (i-C) of the above-described process comprises the de-esterification of compound (VII). This transformation may be accomplished by utilising any conventional de-esterification procedure known from the art.

In a typical embodiment, the de-esterification of compound (VII) may be effected by treatment with an alkaline solution, typically an aqueous solution of an inorganic base, e.g. an alkali metal hydroxide such as lithium hydroxide or sodium hydroxide.

Where $R^1$ in compound (VII) represents optionally substituted benzyl, the de-esterification may suitably be effected by treating compound (VII) with gaseous hydrogen in the presence of a hydrogenation catalyst. The catalyst may be any hydrogenation catalyst known from the art, but will suitably be palladium on carbon. The reaction will conveniently be carried out under an elevated pressure in a suitable solvent, e.g. a lower alkanol such as methanol.

The procedure for obtaining compound (III) in substantially optically pure form from compound (II), as described in steps (i-A), (i-B) and (i-C) above, is a novel process and constitutes a further feature of the present invention.

Furthermore, the procedure for obtaining compound (III) in substantially optically pure form from compound (VI), as described in steps (i-B) and (i-C) above, is a novel process and constitutes a further feature of the present invention.

In an alternative procedure, the compounds of formula (VI) above may be prepared by means of a process which comprises the following steps:

(i-A-α) protection of the amino group of D,L-serine of formula (VIII):

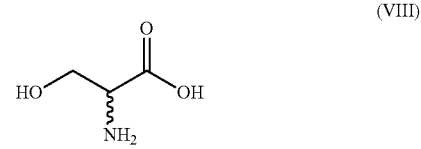

(VIII)

to provide a compound of formula (IX):

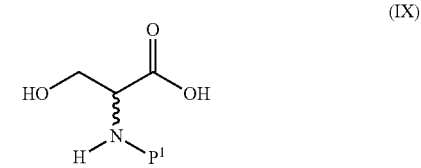

(IX)

wherein $P^1$ represents an N-protecting group;

(i-A-β) O-methylation of the compound of formula (IX) thereby obtained to provide a compound of formula (X):

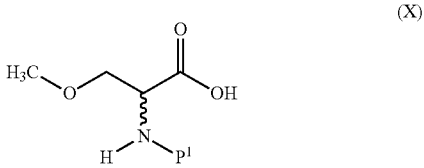

wherein $P^1$ is as defined above;

(i-A-γ) conversion of the compound of formula (X) thereby obtained into an ester derivative of formula (XI):

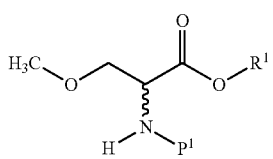

wherein $R^1$ and $P^1$ are as defined above; and (i-A-δ) removal of the N-protecting group $P^1$ from the compound of formula (XI) thereby obtained.

Step (i-A-α) of the above-described process comprises the protection of the amino group of D,L-serine of formula (VIII) above to provide a compound of formula (IX) above.

Protection of the amino group of compound (VIII) may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999.

In a particular embodiment, the N-protecting group $P^1$ is tert-butoxycarbonyl, in which case the preparation of compound (IX) will suitably be effected by treating compound (VIII) with di-tert-butyl dicarbonate, ideally under basic conditions. The reaction may conveniently be carried out in a suitable organic solvent, typically an ethereal solvent, e.g. a cyclic ether such as 1,4-dioxane, optionally in admixture with water, in the presence of a base, typically an inorganic base, e.g. an alkali metal hydroxide such as sodium hydroxide.

Step (i-A-β) of the above-described process comprises the O-methylation of compound (IX) to provide compound (X). The reaction will generally be mediated by treatment of compound (IX) with a methylating agent. Examples of typical methylating agents are described in prior art publications. Such publications include U.S. Pat. No. 5,773,475 and WO 2006/037574.

In a particular embodiment, the methylating agent is dimethyl sulphate. The O-methylation reaction may conveniently be carried out in a suitable organic solvent, e.g. an aromatic hydrocarbon such as toluene, optionally in admixture with water, in the presence of a reagent such as tetrabutylammonium bromide and a base, typically an inorganic base, e.g. an alkali metal hydroxide such as sodium hydroxide.

Step (i-A-γ) of the above-described process comprises the conversion of compound (X) into the ester derivative (XI). This transformation may be achieved by utilising reaction conditions analogous to those described above for the conversion of compound (II) into compound (VI). Thus, compound (X) may suitably be reacted with a compound of formula $R^1$-$L^1$, wherein $R^1$ and $L^1$ are as defined above.

The reaction is conveniently effected under basic conditions, typically in the presence of an inorganic base, suitably an alkali metal carbonate such as potassium carbonate.

Step (i-A-δ) of the above-described process comprises the removal of the N-protecting group $P^1$ from compound (XI).

The deprotection of compound (XI) may be effected by conventional methodology, including techniques analogous to those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999.

Where $P^1$ represents tert-butoxycarbonyl, the deprotection of compound (XI), i.e. the removal of $P^1$, may be achieved by treating compound (XI) with an acid, generally an inorganic acid or an organic acid. In one embodiment, the acid is an inorganic acid. Suitable inorganic acids include mineral acids such as hydrochloric acid. In an alternative embodiment, the acid is an organic acid. A particular organic acid is trifluoroacetic acid.

Step (ii) of the process in accordance with the present invention comprises the acetylation of O-methyl-D-serine (III) to provide compound (IV) in substantially optically pure form. This transformation may be accomplished by utilising any conventional acetylation procedure known from the art. Typically, compound (III) will be treated with an acetylating agent in a suitable organic solvent, optionally in the presence of a reaction promoter.

A suitable acetylating agent may be acetic anhydride or an acetyl halide, e.g. acetyl chloride. Suitable solvents of use in conjunction with the acetylation reaction include halogenated hydrocarbons such as dichloromethane; aromatic heterocycles such as pyridine; and cyclic ethers such as tetrahydrofuran.

A typical promoter for use in conjunction with the acetylation reaction is 4-(dimethylamino)pyridine.

In a particularly advantageous embodiment, the acetylation reaction is effected by treating compound (III) with acetic anhydride in a mixture of tetrahydrofuran and water. Generally, the ratio of tetrahydrofuran to water will be from 4:1 to 16:1 parts by volume. Usually, the ratio of tetrahydrofuran to water will be from 5:1 to 12:1 parts by volume. Typically, the ratio of tetrahydrofuran to water will be from 5:1 to 10:1 parts by volume. Suitably, the ratio of tetrahydrofuran to water will be from 6:1 to 8:1 parts by volume. Ideally, the ratio of tetrahydrofuran to water is in the region of 6:1 parts by volume. By application of these reaction conditions, it has been found that compound (IV) may be obtained in high yield, and high chemical and optical purity.

Step (iii) of the process according to the present invention comprises activating the carboxy group of compound (IV) to provide compound (V) in substantially optically pure form.

The carboxy activating group $Q^1$ in the compounds of formula (V) above may suitably represent halogen, $C_{1-6}$ alkoxy, $(C_{1-6})$alkyl carbonyl oxy or $(C_{1-6})$alkoxycarbonyloxy.

Typical values of $Q^1$ include chloro, methoxy, ethoxy, tert-butoxy, acetoxy and isobutoxycarbonyloxy. In a particular embodiment, $Q^1$ represents isobutoxycarbonyloxy, i.e. —OC(O)OCH$_2$CH(CH$_3$)$_2$.

Conversion of compound (IV) into compound (V) will typically be accomplished utilising conventional methodology well known from the art.

Where $Q^1$ represents isobutoxycarbonyloxy, the reaction typically comprises treating compound (IV) with an isobutyl haloformate, e.g. isobutyl chloroformate. The reaction is conveniently effected in a suitable organic solvent, e.g. a cyclic ether such as tetrahydrofuran, advantageously at a low temperature, e.g. a temperature in the region of −20° C., in the presence of a reagent such as 4-methylmorpholine.

Step (iv) of the process according to the present invention comprises reacting compound (V) with benzylamine. The reaction is conveniently effected in a suitable organic solvent, e.g. a cyclic ether such as tetrahydrofuran, or an organic ester such as ethyl acetate. Advantageously, the reaction will be effected in tetrahydrofuran. Advantageously, the reaction will be performed at a low temperature, e.g. a temperature in the region of −20° C. Ideally, the reaction may be performed directly on the reaction mixture from step (iii), without any need for isolation or purification of the material obtained from step (iii).

After compound (V) has been allowed to react with benzylamine, the reaction mixture is ideally quenched with an acidic solution, suitably an aqueous solution of an inorganic acid, e.g. a mineral acid such as hydrochloric acid, advantageously at a low temperature, e.g. a temperature in the region of −20° C. By proceeding in this manner, it has been found that lacosamide (I) may be obtained in high yield, and high chemical and optical purity.

The procedure for obtaining lacosamide (I) in substantially optically pure form from compound (III), as described in steps (ii), (iii) and (iv) above, is a novel process and constitutes a further feature of the present invention.

In an alternative aspect, the present invention provides a process for the preparation of lacosamide of formula (I), as depicted above, in substantially optically pure form, which comprises the following steps:

(a) acetylation of O-methyl-D,L-serine of formula (II) as depicted above to provide the compound of formula (XII):

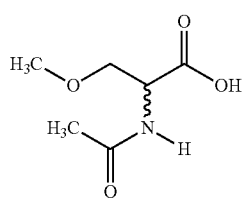

(XII)

(b) resolution of the compound of formula (XII) thereby obtained to provide the compound of formula (IV), as depicted above, in substantially optically pure form;

(c) activating the carboxy group of the compound of formula (IV) thereby obtained, as described for step (iii) above, to provide a compound of formula (V), as depicted above, in substantially optically pure form; and (d) reacting the compound of formula (V) thereby obtained with benzylamine, as described for step (iv) above.

Step (a) of the above-described process comprises the acetylation of O-methyl-D,L-serine (II) to provide compound (XII). This transformation may be accomplished by utilising any conventional acetylation procedure known from the art. Typically, compound (II) will be treated with an acetylating agent in a suitable organic solvent, optionally in the presence of a reaction promoter, under reaction conditions analogous to those described above for the acetylation of compound (III).

Step (b) of the above-described process comprises the resolution of compound (XII) to provide compound (IV) in substantially optically pure form. Resolution may suitably be accomplished by various conventional methods known from the prior art, as described above in relation to step (i).

Suitably, the resolution of compound (XII) may be effected by a biochemical process. A preferred biochemical process is enzymatic resolution. Examples of suitable enzymes of use in the enzymatic resolution procedure include the following:

acylase I from *Aspergillus melleus*
acylase I from porcine kidney
acylase I from *Aspergillus* specie, immobilised on Eupergit®
esterase from porcine liver
esterase from horse liver
esterase from *Bacillus* sp.
lipase from *Rhizopus arrhizus*
lipase from *Aspergillus*
lipase from *Candida antarctica*
lipase from *Rhizopus niveus*
lipase from hog pancreas
lipase from *Penicillium roqueforti*

In a specific embodiment, the enzymatic resolution process may be effected using acylase I from porcine kidney.

The enzymatic resolution procedure is conveniently carried out by contacting compound (XII) with the selected enzyme in an aqueous solution adjusted to a pH of approximately 7.5-8.0, with subsequent elimination of the enzyme. Typically, the pH of the aqueous solution will be adjusted by treatment with a buffer, e.g. a phosphate buffer such as sodium phosphate, or a base, e.g. an alkali metal hydroxide such as sodium hydroxide. Typically, the enzyme will be eliminated by denaturation. The denaturation procedure may suitably be effected by treatment with acid, e.g. a mineral acid such as hydrochloric acid, and injection onto an ion exchange resin such as Dowex™ 50WX4-50. Alternatively, the denaturation procedure may involve heat treatment in a suitable organic solvent, e.g. a $C_{1-4}$ alkanol such as methanol.

In a preferred approach, the enzymatic resolution procedure is effected by contacting compound (XII) with the selected enzyme in an aqueous solution adjusted to a pH of approximately 7.5-8.0; removing the enzyme; and separating the resulting mixture of compound (IV) and O-methyl-L-serine of formula (XIII)

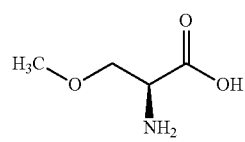

(XIII)

to provide compound (IV) in optically pure form.

As noted above, the pH of the aqueous solution will typically be adjusted by treatment with a buffer, e.g. a phosphate buffer such as sodium phosphate, or a base, e.g. an alkali metal hydroxide such as sodium hydroxide. Ideally, the aqueous solution containing compound (XII) and the selected enzyme will be stirred for 1 to 5 hours.

Removal of the enzyme may be accomplished by any suitable technique known from the art. Typical techniques include chemical precipitation, centrifugation and membrane filtration. As a general rule, centrifugation is faster than filtration, but can lead to increased denaturation of the enzyme. Consequently, the choice of technique to be employed will tend to be dependent upon the balance between speed of execution and the desirability of recycling the enzyme for repeated utilisation. In a selected embodiment, the enzyme is removed by centrifugation. Ideally, the reaction mixture will be acidified prior to centrifugation, typically to a pH in the region of 2 to 3, suitably 2.5. Acidification will typically be accomplished by treating the reaction mixture with a mineral acid, e.g. hydrochloric acid.

Separation of the mixture of compound (IV) and compound (XIII) may also be accomplished by any suitable technique known from the art. Typical procedures include ion exchange chromatography; and salt formation with selective precipitation.

In a preferred embodiment, compounds (IV) and (XIII) are separated by ion exchange chromatography. Suitable ion exchange resins are well known from the art. Ideally, the ion exchange resin to be employed for the separation of compounds (IV) and (XIII) will be an acidic resin. Suitably, the acidic resin will comprise sulfonic acid functional groups. Suitably, the resin will comprise a styrene-divinylbenzene gel matrix. A preferred acidic ion exchange resin, comprising sulfonic acid functional groups and a styrene-divinylbenzene gel matrix, is Dowex™ 50WX4-50. In that case, compound (IV) will be eluted by an acidic eluent, e.g. a mineral acid such as hydrochloric acid; and compound (XIII) will be eluted by a basic eluent, e.g. aqueous ammonia. Acetic acid, obtained from the stereoselective enzymatic deacetylation of compound (XII), will be eluted together with compound (IV) in the acidic phase, and can be removed by standard techniques, e.g. azeotroping with toluene.

In an alternative embodiment, compounds (IV) and (XIII) may be separated by salt formation with selective precipitation. In a particular aspect of that embodiment, the residual acetic acid is first removed from the reaction mixture by conventional means, e.g. azeotroping with toluene; then the pH of the reaction mixture is adjusted to 9 to 12, preferably 9, by treatment with a base, e.g. an alkali metal hydroxide such as sodium hydroxide. To the resulting mixture is added an acid, preferably an organic acid such as L-tartaric acid. After concentration to dryness, the residue is taken up in a suitable solvent, typically a $C_{1-4}$ alkanol such as ethanol or isopropanol, preferably isopropanol; and the resulting slurry is stirred for an appropriate time, typically about 30 minutes, ideally at ambient temperature. The L-tartrate salt of compound (XIII) crystallises preferentially, and the resulting precipitate can accordingly be filtered off and removed. The filtrate is enriched in the desired product of formula (IV) in optically pure form.

Compound (XIII) need not be wasted. It can be recycled back into compound (XII). In one approach, compound (XIII) can be converted into compound (XII) by means of a process which comprises the following steps:

(b-1A) acetylation of compound (XIII) as depicted above to provide the compound of formula (XIV):

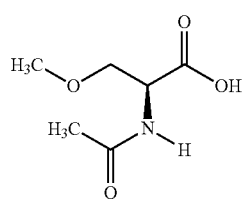

(XIV)

in substantially optically pure form; and (b-1B) racemisation of the compound of formula (XIV) thereby obtained to provide the compound of formula (XII) as depicted above.

Step (b-1A) of the above-described process comprises the acetylation of compound (XIII) to provide compound (XIV). This transformation may be accomplished by methods analogous to those described for step (ii) above in relation to the acetylation of compound (III).

Step (b-1B) of the above-described process comprises the racemisation of compound (XIV) to provide compound (XII). This transformation may be accomplished by utilising any conventional racemisation procedure known from the art. Typically, compound (XIV) will be treated with a suitable acidic or basic reagent. In a particular method, compound (XIV) can be racemised by treatment with acetate anion generated in situ in step (b-1A) when compound (XIII) is treated with acetic anhydride.

In an alternative approach, compound (XIII) can be converted into compound (XII) by means of a process which comprises the following steps:

(b-2A) racemisation of compound (XIII) as depicted above to provide O-methyl-D,L-serine of formula (II) as depicted above; and (a) acetylation of O-methyl-D,L-serine of formula (II) thereby obtained to provide the compound of formula (XII), as described above.

Step (b-2A) of the above-described process comprises the racemisation of compound (XIII) to provide compound (II). This transformation may be accomplished by utilising any conventional racemisation procedure known from the art. Typically, compound (XIII) will be treated with a suitable acidic or basic reagent. In a particular method, compound (XIII) can be racemised by treatment with an inorganic base, e.g. an alkali metal hydroxide such as sodium hydroxide. The racemisation reaction will conveniently be effected at a temperature in excess of 65° C., ideally at 100° C.

The procedure for obtaining compound (IV) in substantially optically pure form from compound (II), as described in steps (a) and (b) above, is a novel process and constitutes a further feature of the present invention.

In a further procedure, compound (IV) above may be prepared in substantially optically pure form from a compound of formula (VII) as defined above by means of a process which comprises the following steps:

(α) acetylation of a compound of formula (VII) as defined above to provide a compound of formula (XV):

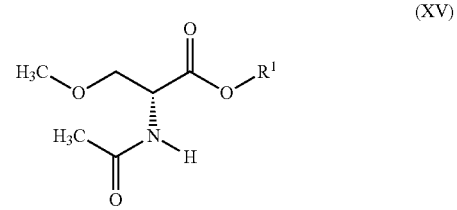

(XV)

wherein $R^1$ is as defined above; in substantially optically pure form; and (β) de-esterification of the compound of formula (XV) thereby obtained.

Step (α) of the above-described process comprises the acetylation of compound (VII) to provide compound (XV). This transformation may be accomplished by methods analogous to those described for step (ii) above in relation to the acetylation of compound (III).

Step (β) of the above-described process comprises the de-esterification of compound (XV) to provide compound (IV) in substantially optically pure form. This transformation may be accomplished by methods analogous to those described for step (i-C) above in relation to the de-esterification of compound (VII).

The procedure for obtaining compound (IV) in substantially optically pure form from compound (VII), as described in steps (α) and (β) above, is a novel process and constitutes a further feature of the present invention.

Following repeated experimental runs of the process in accordance with the present invention, a characteristic by-product has been detected as an impurity which is produced alongside the desired product lacosamide (I), even after several crystallisations (i.e. at least two crystallisations) of the final product. The chemical structure of the by-product is as depicted in formula (XVI) below:

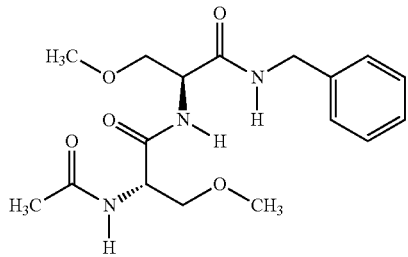

(XVI)

It is believed that the by-product of formula (XVI) above is formed by dimerisation of certain intermediates present in the reaction vessel under the prevailing reaction conditions.

The present invention accordingly provides the reaction product of the above-described process containing a detectable amount of the by-product of formula (XVI) above. By "detectable amount" is meant typically up to 1.0%, suitably up to 0.5%, generally up to 0.4%, preferably up to 0.3%, more preferably up to 0.2%, still more preferably up to 0.1%, yet more preferably up to 0.05%, most preferably up to 0.01%.

The by-product of formula (XVI) above is a novel compound and constitutes a further feature of the present invention.

It has also been found that lacosamide (I) can be prepared in substantially optically pure form from compound (III) above by a process which comprises the following steps:

(A) reaction of O-methyl-D-serine of formula (III), as depicted above, with phosgene;

(B) reacting the product thereby obtained with benzylamine, to provide the compound of formula (XVII):

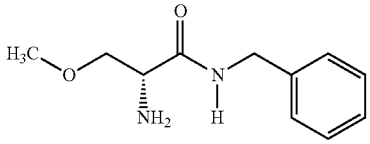

(XVII)

in substantially optically pure form; and (C) acetylation of the compound of formula (XVII) thereby obtained.

Step (A) of the above-described process comprises reacting compound (III) with phosgene. Suitably, compound (III) will be reacted with gaseous phosgene or with triphosgene.

The reaction may conveniently be effected in a suitable organic solvent, typically an ethereal solvent such as tetrahydrofuran or diethyl ether.

Step (B) of the above-described process is a benzylation reaction, which may suitably be effected by utilising reaction conditions analogous to those described in step (iv) above for the benzylation of compound (V).

Step (C) of the above-described process comprises the acetylation of compound (XVII) to provide lacosamide (I). This transformation may be accomplished by utilising any conventional acetylation procedure known from the art. Typically, compound (XVII) will be treated with an acetylating agent in a suitable organic solvent, optionally in the presence of a reaction promoter, under reaction conditions analogous to those described above for the acetylation of compound (III).

The following non-limiting Examples are intended to illustrate the present invention.

EXAMPLE 1

O-Methyl-D-serine (Method 1)

Into a 250 mL round-bottomed flask equipped with a stirrer, reflux condenser and thermometer was added O-methyl-D,L-serine (5 g) in 90:10 methanol/water (25 mL). N-Acetyl-D-phenylalanine (8.70 g) was added in one portion and the mixture heated to 50° C. overnight. The suspension was cooled to room temperature and filtered, and the solid was rinsed with 90:10 methanol/water (5 mL) and dried at 40° C. under vacuum for 3 h. The N-acetyl-D-phenylalanine salt of O-methyl-D-serine (3.4 g, 25%) was obtained as a white solid with a chiral purity >90%. Regeneration of the title compound could be effected by adjustment of the pH to 1-2 by treatment with HCl, followed by extraction into an organic solvent and subsequent adjustment of the pH to ~7 with NaOH.

EXAMPLE 2

O-Methyl-D-Serine (Method 2)

Into a 250 mL round-bottomed flask equipped with a stirrer, reflux condenser and thermometer was added O-methyl-D,L-serine (5 g) in ethanol (150 mL). N-Acetyl-(R)-naphthylalanine (10.80 g) was added in one portion and the mixture heated to 50° C. overnight. The suspension was cooled to room temperature and filtered, and the solid was rinsed with ethanol (5 mL) and dried at 40° C. under vacuum for 3 h. Crude N-acetyl-(R)-naphthylalanine salt of O-methyl-D-serine (6.4 g, 40.5%) was obtained as a white solid with a chiral purity >90%. A portion (5 g) of this solid was suspended in ethanol (30 mL), heated to 50° C. for 4 h, cooled to room temperature and filtered. The resulting solid was rinsed with ethanol (5 mL) and dried at 40° C. under vacuum for 3 h. Pure N-acetyl-(R)-naphthylalanine salt of O-methyl-D-serine (4.6 g, 91.5%) was obtained as a white solid with a chiral purity >95%. Regeneration of the title compound could be effected by adjustment of the pH to 1-2 by treatment with HCl, followed by extraction into an organic solvent and subsequent adjustment of the pH to ~7 with NaOH.

EXAMPLE 3

O-Methyl-D,L-Serine Benzyl Ester

To a slurry of D,L-serine (500 g, 4.76 mol) in 1,4-dioxane (2.5 L) at 0-5° C. was slowly added a solution of sodium hydroxide (400 g, 10 mol) in water (2.5 L), followed by dicarbonate (1639 mL, 7.14 mol). The temperature was then raised to 25-27° C., and the reaction mixture was maintained at that temperature overnight. The solvent was evaporated under reduced pressure to approximately one-third of the total reaction mass, then the reaction mixture was filtered through Celite® to remove the salts. The aqueous layer was washed with ethyl acetate (2×2.5 L), cooled to 0-5° C., then acidified with a solution of citric acid (4.4 kg, 23.15 mol) in water (3.6 L), and the pH was adjusted to ~2. The residue was extracted with ethyl acetate (5×2.5 L), then the combined organic layers were washed with brine (1 L) and dried over sodium sulphate. The solvent was evaporated under reduced pressure to afford a pale yellow viscous liquid (925 g, 94.7%). HPLC purity: 78.03%.

To a mixture of this material (500 g, 2.4 mol) in toluene (2.5 L) was added tetrabutylammonium bromide (39.2 g). The reaction mixture was cooled to 0-5° C., then dimethyl sulphate (946.5 mL, 9.7 mol) and a solution of sodium hydroxide (878 g, 21.9 mol) in water (2.17 L) were simultaneously added at 0-5° C. The reaction mixture was maintained at 0-5° C. for 30 minutes, then the temperature was raised to 25-27° C. and the reaction mixture was maintained at that temperature overnight. The reaction mixture was allowed to settle, and separated into two layers. The aqueous layer was washed with toluene (2.5 L), cooled to 0-5° C., then acidified with a solution of citric acid (1.85 kg, 9.7 mol) in water (1.34 L), to pH ~3 at 0-5° C. The residue was extracted with dichloromethane (6×2.5 L), then the combined organic layers were washed with brine (1.8 L) and dried over sodium sulphate. The solvent was evaporated under vacuum to afford an off-white solid (281 g, 52.6%). HPLC purity: 81.1%.

To a mixture of this material (385 g, 1.75 mol) in acetone (1925 mL) was added potassium carbonate (358 g, 2.6 mol) slowly at 0-5° C., followed by slow addition of benzyl bromide (210 mL, 1.75 mmol). The temperature was maintained at 0-5° C. for 30 minutes, then raised to 25-27° C. and the reaction mixture was maintained at that temperature overnight. The reaction mass was filtered to remove the inorganic salts, and the salts were then washed with acetone. The solvent was evaporated under reduced pressure and the residue was dissolved in ethyl acetate. The ethyl acetate layer was washed twice with water, followed by brine. The organic layer was dried over sodium sulphate. The solvent was evaporated completely to provide a brick red-coloured liquid (540 g, 98.7%).

To a mixture of this material (300 g, 0.97 mol) in tetrahydrofuran (1.5 L) at 0-5° C. was slowly added a solution of conc. hydrochloric acid (793 mL) in water (1.6 L). The temperature was maintained at 0-5° C. for 30 minutes, then raised to 25-27° C. and the reaction mixture was maintained at that temperature for 30 h. The solvent was evaporated completely and the aqueous layer was washed five times with dichloromethane. The aqueous layer was basified (pH ~10) with sodium carbonate (700 g) at 0-5° C. The residue was extracted four times into dichloromethane, and the organic layer was dried over sodium sulphate. The solvent was evaporated completely under vacuum to afford the title compound (122 g, 60%) as a pale yellow liquid. HPLC purity: 95.17%.

EXAMPLE 4

O-Methyl-D-Serine (Method 3)

To a solution of O-methyl-D,L-serine benzyl ester (50 mg, 0.239 mol) in 4-methyl-2-pentanone (500 mL) was added N-acetyl-L-methionine (45.7 g, 0.239 mol) at 25° C. The reaction mixture was heated to 50° C. and stirred for 2 hours, then allowed to cool to 25° C. and stirred for 16 hours at 25-30° C. The resulting solid material was filtered and dried at 60° C. for 3 hours. The mother liquors were evaporated. The isolated solid material (66 g) was dissolved in water (132 mL) at 25° C. The aqueous solution was basified with aqueous $Na_2CO_3$ solution (1M; 0.28 mol) at 5-10° C. The reaction mixture was extracted with dichloromethane (3×330 mL) at 25-30° C. The organic layer was dried over $Na_2SO_4$ and the solvent was evaporated under reduced pressure to afford O-methyl-D-serine benzyl ester as a light brown liquid (32.6 g, 66%). Chiral purity: 94.6%. Chemical purity: 98.3%.

Into a Parr hydrogenator under a nitrogen atmosphere was charged a solution of O-methyl-D-serine benzyl ester (30 g, 0.143 mol) in methanol (210 mL). A slurry of 10% Pd—C (50% wet; 3.9 g, 13% w/w) in methanol (90 mL) was slowly added. The equipment was flushed with hydrogen gas, then a 50 psi pressure of hydrogen was maintained for 45 minutes. Water was added into the reaction mass to dissolve the solid material. The reaction mixture was filtered through celite and washed with methanol (150 mL) and water (30 mL). The solvent was evaporated under reduced pressure to afford crude product (16.6 g). A slurry was made from a portion (14 g) of the resulting material in acetone. The slurry was stirred for 2 hours at 25° C., then filtered. The wet filter cake was washed with acetone. The residue was dried at 50° C. for 1 hour, to afford the title compound (13 g, 90.2%). Chiral HPLC: 93.5%. Chemical HPLC: 96.8%.

EXAMPLE 5

(R)-2-Acetylamino-3-Methoxypropionic Acid (Method 1)

To a suspension of O-methyl-D-serine (12 g, 0.1 mol) in tetrahydrofuran (72 mL) and water (12 mL) was added acetic anhydride (9.53 mL, 0.1 mol) over a period of 15 minutes at 20° C. The temperature was maintained at 20° C. for 4 hours. The solvent was completely evaporated from the reaction mixture at 50° C. The reaction mixture was then subjected to co-distillation with toluene (3×60 mL) at 60° C., to afford crude solid material (16 g). Toluene (60 mL) was added and the contents were stirred for 1 hour at 25-27° C., then filtered. The wet filter cake was washed with toluene. The residue was dried under suction for 15 minutes, then dried under vacuum at 50° C. to constant weight, to give the title compound (14.7 g, 93.4%). Chiral HPLC: 93.0%. Chemical HPLC: 97.4%.

EXAMPLE 6

N-Acetyl-O-Methyl-D,L-Serine

Into a vessel, equipped with a mechanical stirrer, was added O-methyl-D,L-serine (1.0 eq.) at 20° C. Tetrahydrofuran (6 volumes) and water (0.65 volume) were added. Acetic anhydride (1.2 eq.) was added dropwise over 5 minutes. The white suspension was stirred mechanically until complete conversion was observed by HPLC monitoring (approximately 16 h), by which time the reaction mixture had become homogeneous. The tetrahydrofuran and water were removed azeotropically. Toluene was added in order to effect complete removal of water and acetic acid (KF and GC control). The wet solid was dried at 40° C. under vacuum overnight. The title compound (90% yield)

was obtained as a white solid with a chemical purity of >98% as measured by HPLC.

EXAMPLE 7

(R)-2-Acetylamino-3-Methoxypropionic Acid
(Method 2)

In a vessel, equipped with a magnetic stirrer and pH controller, N-acetyl-O-methyl-D,L-serine (3 g) was dissolved in demineralized water (30 mL) and the pH was adjusted to 7.5-8.0 with 5N sodium hydroxide solution. Acylase I from Porcine Kidney (EC: 3.5.1.14) (50 mg) was added and the solution maintained at 25° C. under mild agitation overnight. The pH was adjusted to 2.7 with concentrated HCl and the aqueous solution injected onto Dowex™ 50WX4-50 ion exchange resin (50 mL) conditioned at pH 3.8. The resulting material was eluted with water at pH 2.4. The aqueous solution thereby obtained was then evaporated to dryness under vacuum to afford the title compound (1.5 g, 50%) as an off-white solid.

EXAMPLE 8

(R)-2-Acetylamino-N-benzyl-3-methoxypropionamide
(Method 1)

To a suspension of (R)-2-acetylamino-3-methoxypropionic acid (5 g, 31.05 mmol) in tetrahydrofuran (50 mL), under a nitrogen atmosphere at −20° C., was added isobutyl chloroformate (4.04 mL, 31.05 mmol) over a period of 10 minutes. The temperature was maintained at −20° C. for 10 minutes. 4-Methylmorpholine (3.42 mL, 31.05 mmol) was added over a period of 10 minutes, and the temperature was maintained for a further 10 minutes. Benzylamine (3.39 mL, 31.05 mmol) was added directly into the reaction mixture via a syringe at −20° C. over a period of 10 minutes. The temperature of the reaction mixture was maintained at −20° C. for a further 20 minutes. The reaction mixture was quenched with aqueous HCl (1M; 21.88 mL). Solvent was removed by evaporation at 45-50° C., and crude material (16 g) was isolated. Ethyl acetate (50 mL) was added, and the reaction mixture was washed with water (2×2.5 mL). The organic layer was dried over sodium sulphate and the solvent was completely removed by evaporation to give crude material (5.77 g). A portion (5.5 g) of this material was dissolved in ethyl acetate (50 mL) at 50-55° C. The temperature was maintained for 10 minutes, before cooling to 25° C. After stirring at this temperature for 2 hours the reaction mixture was filtered. The wet filter cake was washed with ethyl acetate (2.5 mL). The residue was dried under suction for 20 minutes, then dried under vacuum at 40° C. to constant weight, to give the title compound (1.38 g, 18.5%). Chiral purity: 99.2%. Chemical HPLC: 96.8%.

EXAMPLE 9

(R)-2-Acetylamino-N-benzyl-3-methoxypropionamide
(Method 2)

(R)-2-Acetylamino-3-methoxypropionic acid (8.06 g, 0.05 mol) was dissolved in tetrahydrofuran (80 mL). Isobutyl chloroformate (7.8 mL, 0.06 mol) was added at −10° C. within 10 minutes, followed by 4-methylmorpholine (6.6 mL, 0.06 mol), and the mixture was stirred at −10° C. for 40 minutes. A solution of benzylamine (6.55 mL, 0.06 mol) in tetrahydrofuran (10 mL) was then added at −10° C. The mixture was allowed to warm to room temperature, the solvent evaporated and the residue dissolved in dichloromethane. The solution was successively washed with water (30 mL), 1M HCl (30 mL), 5% sodium hydrogencarbonate solution (30 mL) and again with water (30 mL). The solvent was evaporated and the residue crystallized in ethyl acetate to afford the title compound (7.09 g, 57%). LCMS analysis: 98.0%.

EXAMPLE 10

(R)-2-Acetylamino-N-benzyl-3-methoxypropionamide
(Method 3)

O-Methyl-D-serine (1.19 g, 0.01 mol) was suspended in tetrahydrofuran (40 mL). The suspension was heated to reflux and treated dropwise with a solution of triphosgene (1.09 g) and tetrahydrofuran (30 mL). The residual cloudiness dispersed into solution. The reaction mixture was stirred overnight at room temperature, then filtered to clarity. The solvent was completely removed by rotary evaporation to afford an oil (1.06 g, 73.7%). This material was dissolved in ethyl acetate (20 mL) and treated with benzylamine (0.78 g) at room temperature. The reaction mixture was stirred for 2 hours and then washed with water (2×3 mL). The solvent was completely removed from the organic phase by rotary evaporation to afford an oil (1.12 g). The resulting crude material was dissolved in dichloromethane (25 mL). After the addition of acetic anhydride (0.82 g, 0.08 mol), the reaction mixture was stirred for 2 hours at room temperature. The reaction mixture was successively extracted with water (5 mL), 1M hydrochloric acid (5 mL), 5% aqueous sodium hydrogencarbonate solution (5 mL) and water (5 mL). The solvent was completely removed from the organic phase by rotary evaporation to afford the title compound (1.20 g, 88.9%) as a colourless crystalline solid. HPLC: 93.46% (R) isomer.

EXAMPLE 11

(R)-2-Acetylamino-N-benzyl-3-methoxypropionamide
(Method 3)

N-Acetyl-O-methyl-D,L-serine (10 g, 62.1 mmol) was placed in a glass reactor and fresh demineralised water (90 mL) was added. Freshly prepared 5M aqueous sodium hydroxide solution (approx. 11.5 mL) was added to adjust the reaction mixture to pH 8. Acylase I from Porcine Kidney (EC: 3.5.1.14; grade I) (0.1 g) was added, and the homogeneous solution was stirred mechanically at 100 r.p.m. at 25° C. for 1 h. Molar conversion of N-acetyl-O-methyl-D,L-serine (400 MHz $^1$H NMR, $D_2O$): ~94%. Enantiomeric excess of O-methyl-L-serine (HPLC): ~99%.

HCl (6M; 10% v/v) was added to the reaction mixture, which was placed in Falcon centrifuge tubes. The tubes were centrifuged at 10,000 r.p.m for 10 minutes at 25° C. The precipitated enzyme was recovered. Final pH of reaction mixture: ~2.5. Recovery of enzyme: ~100%.

To wet Dowex™ 50WX4-50 ion exchange resin (1 volume) was added HCl (pH 3.6) in order to obtain a slurry (orange supernatant). The slurry was transferred onto a glass chromatography column. The volume of the resin in the column, known as the Bed Volume (BV), corresponded to approximately 1.15 times the volume of wet resin. The column was eluted (approx. 4 BV) until a colourless eluate was obtained. Freshly centrifuged reaction mixture (0.375 volumes compared with wet resin) was added at a rate of 5-6 mL per minute. The column was then eluted with HCl (pH 3.6; ~3.3 BV) at a rate of 5-6 mL per minute, to provide a solution of title compound. Next, the column was eluted with demineralised water (~7 BV) at a rate of 6-7 mL per minute until the pH was about 6.5. Subsequently, the column was eluted with ammonia (1M; 3.3 BV), to provide a solution of O-methyl-L-serine.

The solution of O-methyl-L-serine was concentrated by rotary evaporation at 40° C. under maximum vacuum, to afford C)-methyl-L-serine as a white solid. Crude yield: 94.9%. No racemisation.

The solution of title compound was evaporated. To remove residual acetic acid, excess toluene (0.13 volumes compared with wet resin) was added, and the resulting solution was evaporated at 40° C. under maximum vacuum. The addition of toluene and evaporation was repeated, to afford the title compound as a light yellow solid. Crude yield: 94.7%. No racemisation.

EXAMPLE 12

(R)-2-Acetylamino-N-benzyl-3-methoxypropionamide (Method 4)

The enzyme-free reaction mixture obtained from Example 11, second paragraph, was azeotroped with toluene to remove residual acetic acid. To the resulting material was added a 5M aqueous solution of sodium hydroxide to adjust to pH 9. L-Tartaric acid (0.6 equivalents) was added, and the reaction mixture was concentrated to dryness by rotary evaporation at 60° C. under maximum vacuum. Isopropanol (10 volumes) was added, and the resulting slurry was magnetically stirred for approximately 30 minutes at room temperature. The suspension was filtered under vacuum through a sintered glass. The filtrate was concentrated by rotary evaporation, to afford the title compound as a yellow oil. Crude yield: 43%. $^1$H NMR (400 MHz, D$_2$O): 77.5 mol % title compound and 22.5 mol % O-methyl-L-serine.

The invention claimed is:

1. A process for the preparation of lacosamide of formula (I):

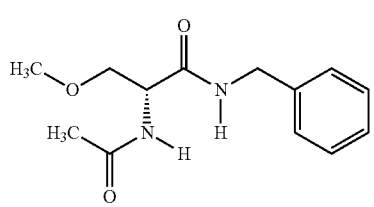

(I)

in at least 95% optically pure form, which process comprises, (ii) acetylating O-methyl-D-serine of formula (III),

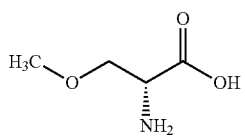

(III)

to provide the compound of formula (IV),

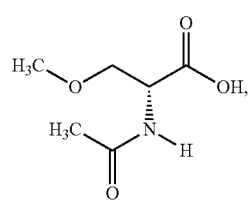

(IV)

in at least 95% optically pure form;

(iii) activating the carboxy group of the compound of formula (IV) thereby obtained to provide a compound of formula (V),

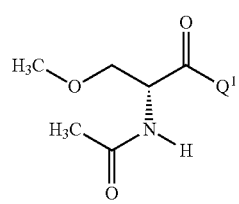

(V)

wherein Q$^1$ is a carboxy activating group; and (iv) reacting the compound of formula (V) thereby obtained with benzylamine.

2. The process as claimed in claim 1 wherein, in part (ii), the acetylation reaction is effected by treating compound (III) with acetic anhydride in a mixture of tetrahydrofuran and water.

3. The process as claimed in claim 2 wherein the ratio of tetrahydrofuran to water is in the region of 6:1 parts by volume.

4. The process as claimed in claim 1 wherein Q$^1$ represents isobutoxycarbonyloxy.

5. The process as claimed in claim 1 wherein, in part (iv), the reaction between compound (V) and benzylamine is effected in tetrahydrofuran at a low temperature; followed by quenching with an acidic solution at a low temperature.

6. The reaction product of the process as claimed in claim 1 containing up to 1% of the compound of formula (XVI):

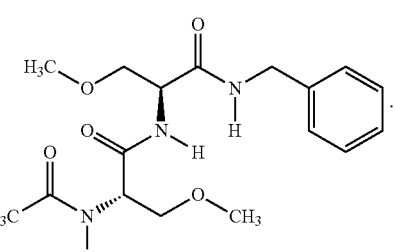

(XVI)

* * * * *